(12) United States Patent
Dixon

(10) Patent No.: US 9,132,114 B2
(45) Date of Patent: Sep. 15, 2015

(54) COMPOSITION AND METHOD TO TREAT WOUNDS

(76) Inventor: David M. Dixon, Tucson, AZ (US)

( * ) Notice: Subject to any disclaimer, the term of this patent is extended or adjusted under 35 U.S.C. 154(b) by 976 days.

(21) Appl. No.: 12/375,521

(22) PCT Filed: Jul. 30, 2007

(86) PCT No.: PCT/US2007/074765
§ 371 (c)(1),
(2), (4) Date: Jan. 28, 2009

(87) PCT Pub. No.: WO2008/014518
PCT Pub. Date: Jan. 31, 2008

(65) Prior Publication Data
US 2009/0324578 A1  Dec. 31, 2009

Related U.S. Application Data

(60) Provisional application No. 60/834,130, filed on Jul. 28, 2006.

(51) Int. Cl.
*A61K 36/00* (2006.01)
*A61K 31/245* (2006.01)
*A61K 31/70* (2006.01)
*A61K 36/02* (2006.01)
*A61K 45/06* (2006.01)

(52) U.S. Cl.
CPC ............... *A61K 31/245* (2013.01); *A61K 31/70* (2013.01); *A61K 36/02* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,659,572 A * | 4/1987 | Murray | ......................... 424/448 |
| 4,767,619 A | 8/1988 | Murray | |
| 5,051,256 A | 9/1991 | Barnes | |
| 2004/0029829 A1 | 2/2004 | Miyazaki et al. | |
| 2005/0112151 A1 * | 5/2005 | Horng | ........................... 424/401 |
| 2006/0223730 A1 * | 10/2006 | Neuls et al. | .................... 510/156 |
| 2007/0248563 A1 * | 10/2007 | Iovanni et al. | ................... 424/74 |
| 2007/0292459 A1 * | 12/2007 | Cooper et al. | ................ 424/401 |

FOREIGN PATENT DOCUMENTS

| FR | 2773077 A1 * | 7/1999 |
|----|--------------|--------|
| GB | 1242083 A * | 8/1971 |
| GB | 2336536 A * | 10/1999 |
| IL | 156349 | 6/2003 |

OTHER PUBLICATIONS

Vidal et al, Enhanced DNA extraction and PCR amplification of SSU ribosomal genes from crustose coralline algae, Journal of Applied Phycology, (Jun. 2002) vol. 14, No. 3, pp. 223-227.*

* cited by examiner

*Primary Examiner* — Qiuwen Mi
(74) *Attorney, Agent, or Firm* — Dale F. Regelman; Quarles & Brady LLP

(57) ABSTRACT

A composition to treat wounds comprising non-geniculate marine coral algae in combination with one or more sugars.

10 Claims, 2 Drawing Sheets

FIG. 1

| | Corralline Algae | Sugar(s) | Carrier | Complexing Polymer | Iodine | Hydrophilic Compound | Hydrocolloid | Anesthetic |
|---|---|---|---|---|---|---|---|---|
| Lower Limit (Wt. %) | 0.5 | 1 | 0 | 0 | 0 | 0 | 0 | 0 |
| Upper Limit (Wt. %) | 99 | 99.5 | 80 | 35 | 40 | 85 | 85 | 20 |

FIG. 2

| ANALYTE | UNITS | LEVEL | ANALYTE | UNITS | LEVEL |
| --- | --- | --- | --- | --- | --- |
| Aluminum | ppm | 1420 | Mecury | ppm | 0.011 |
| Antimony | ppm | 4.57 | Molybdenum | ppm | <0.1 |
| Arsenic | ppm | 0.11 | Neodymium | ppm | 3.51 |
| Barium | ppm | 5.57 | Nickel | ppm | 0.074 |
| Beryllium | ppm | 0.081 | Niobium | ppm | <0.1 |
| Bismuth | ppm | 2.19 | Osmium | ppm | <0.05 |
| Boron | ppm | 12.1 | Palladium | ppm | <0.05 |
| Bromine | ppm | 11.5 | Phosphorus | ppm | 169. |
| Cadmium | ppm | <0.03 | Platinum | ppm | <0.05 |
| Calcium | ppm | 279,000 | Potassium | ppm | 427. |
| Carbon | ppm | 124,000 | Praseodymium | ppm | 0.63 |
| Cerium | ppm | 2.11 | Rhenium | ppm | <0.2 |
| Cesium | ppm | 2.66 | Rhodium | ppm | <0.05 |
| Chloride | ppm | 2370. | Rubidium | ppm | 27.6 |
| Chromium | ppm | 5.10 | Ruthenium | ppm | 0.055 |
| Cobalt | ppm | 0.107 | Samarium | ppm | 0.67 |
| Copper | ppm | 1.59 | Scandium | ppm | 0.685 |
| Dysprosium | ppm | 1.15 | Selenium | ppm | 0.060 |
| Erbium | ppm | 18.9 | Silica | ppm | 28,000 |
| Europium | ppm | <0.1 | Silver | ppm | 1.78 |
| Fluoride | ppm | 7.55 | Sodium | ppm | 3970. |
| Gadolinium | ppm | 3.04 | Strontium | ppm | 2190. |
| Gallium | ppm | 1.27 | Sulfur | ppm | 940. |
| Germanium | ppm | 3.08 | Tantalum | ppm | <0.05 |
| Gold | ppm | <0.05 | Tellurium | ppm | 0.066 |
| Hafnium | ppm | <0.1 | Terbium | ppm | <0.2 |
| Holmium | ppm | <0.1 | Thallium | ppm | 0.33 |
| Indium | ppm | 0.17 | Thorium | ppm | 0.081 |
| Iodine | ppm | 10.6 | Thulium | ppm | <0.05 |
| Iridium | ppm | <0.05 | Tin | ppm | 0.197 |
| Iron | ppm | 10,100. | Titanium | ppm | 31.1 |
| Lanthanum | ppm | 0.314 | Tungsten | ppm | <0.05 |
| Lead | ppm | 0.061 | Vandaium | ppm | 12.9 |
| Lithium | ppm | 3.90 | Ytterbium | ppm | 0.237 |
| Lutetium | ppm | 0.310 | Yttrium | ppm | 1.74 |
| Magnesium | ppm | 99,800 | Zinc | ppm | 16.2 |
| Manganese | ppm | 90.5 | Zirconium | ppm | 0.642 |

Bacteria    counts/100 g    6

< = no quantities of this analyte detected above the stated limit.

COMPOSITION AND METHOD TO TREAT WOUNDS

CROSS REFERENCE TO RELATED APPLICATIONS

This Application claims priority from a U.S. Provisional Application having Ser. No. 60/834,130 filed on Jul. 28, 2006.

FIELD OF THE INVENTION

This invention relates to a composition and method to treat wounds.

BACKGROUND OF THE INVENTION

It is known in the art to treat wounds with one or more sugars. U.S. Pat. No. 4,401,651 teaches a method to treat wounds using a paste formed from sucrose and one or more carriers. Such carriers included agar, cold cream, corn oil, cottonseed oil, gelatin, glycerin, lanolin, olive oil, peanut oil, polyethylene glycol, and the like.

SUMMARY OF THE INVENTION

Applicant's invention comprises a composition, and method using that composition, to treat a variety of chronic non-healing wounds such as burns, pressure/bed sores, diabetic leg and foot ulcers, decubitus ulcers, surgical wound dehiscence, arteriosclerotic ulcers, ischaemic ulcers, postburn ulcers, non-healing lacerations, traumatic ulcers, amputee stumps, chronic or re-occurring wounds, venous stasis ulcers, sickle cell ulcers, scleroderma ulcers, and the like. Applicant's composition comprises non-geniculate marine coral algae in combination with one or more sugars, and in optional combination with one or more carriers, and/or iodine, and/or an iodine-complexing polymer, and/or a moisture absorber, and/or a local anesthetic.

BRIEF DESCRIPTION OF THE DRAWINGS

The invention will be better understood from a reading of the following detailed description taken in conjunction with the drawings in which like reference designators are used to designate like elements, and in which:

FIG. 1 table that recites weight percentages for the components of Applicant's composition; and FIG. 2 recites the components disposed in Applicant's non-geniculate marine coral algae.

DETAILED DESCRIPTION OF THE PREFERRED EMBODIMENTS

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Applicant's invention comprises a composition, and method using that composition, to treat a variety of chronic non-healing wounds such as burns, pressure/bed sores, diabetic leg and foot ulcers, decubitus ulcers, surgical wound dehiscence, arteriosclerotic ulcers, ischaemic ulcers, postburn ulcers, non-healing lacerations, traumatic ulcers, amputee stumps, chronic or re-occurring wounds, venous stasis ulcers, sickle cell ulcers, scleroderma ulcers, and the like.

In certain embodiments, Applicant's composition comprises Coralline Algae or Coral in combination with one or more sugars, and in optional combination with one or more carriers. By "Coralline Algae," Applicant means a non-geniculate marine coral algae. In certain embodiments, such Coralline Algae grows off the coast of Brazil. By "coral", Applicant means: any of numerous chiefly colonial marine polyps of the class Anthozoa that secrete calcareous skeletons to form a rock like deposit; and coral secretions of the genus *Corallium* often used to make jewelry or ornaments.

FIG. 2 recites the elements comprising Coralline Algae. To perform the analysis recited in FIG. 2, the sample was diluted as necessary in glass Class A volumetric flasks. The elements Chloride, Fluoride, and Bromine were analyzed via Ion Chromatography. Cold Vapor Atomic Absorption was used for analysis of Mercury. Graphite Furnace Atomic Absorption was the method used to determine Arsenic, Selenium, Lead and Antimony. Semi-quantitative analysis for all other elements was carried out using Inductively Coupled Plasma-Optical Emission Spectrometry.

Coralline Algae is unique in that it breaks off of its host algae naturally with subsequent minimal environmental impact. Spherical aggregates of such Coralline Algae are gathered after rolling up onto a beach area and then ground into a powder. That powder has been later used as a fertilizer or additive for chicken feed. If the spherical aggregates are not prompted gathered, the coral simply disintegrates and remains as a fine sand that forms a sandy "coral" beach.

Coralline Algae comprises a material which is considered vegan because it lives off Seaweed in Seaweed forests offshore. The powders derived from Coralline Algae comprise up to about 75 minerals with calcium and magnesium predominating.

Applicant has found that Coralline Algae powder comprises a bactericide, a fungicide, and a viricide. In addition, Applicant has found that the calcium and magnesium provided by the coral are utilized as an external source of nutritional building blocks for the metabolism of a recovering wound surface.

It is known in the art to treat wounds with a mixture of sugar and an iodine complex in water. As those skilled in the art will appreciate, such an iodine-containing aqueous composition is sold in commerce under the generic name of povidone-iodine, and under the specific trade name BETADINE. Applicant has found that much if not all of the iodine in the sugar/iodine composition can be replaced by Coralline Algae without diminishing the wound healing capabilities. As those skilled in the art will appreciate, it is well known that topical application of Iodine-containing formulations can cause skin irritation and/or allergic responses.

Applicant has further found that treating wounds with a composition comprising sugar and Coralline Algae actually improves the healing time compared with use of the prior art formulations. More specifically, Applicant has found that the average healing time was decreased by 15% in a group of patients treated with an embodiment of Applicants' composition wherein 1-5%, by weight of the iodine mixture, i.e. BETADINE, was replaced with an equivalent weight of powdered Coralline Algae.

The average healing time was decreased by 35% in a group of patients treated with an embodiment of Applicants' composition wherein 5-25%, by weight, of the BETADINE was replaced with an equivalent weight of powdered Coralline Algae. The average healing time was decreased by 30% in a group of patients treated with an embodiment of Applicants' composition wherein 25-50%, by weight, of the BETADINE was replaced with an equivalent weight of powdered Coralline Algae.

The average healing time was decreased by 15% in a group of patients treated with an embodiment of Applicants' Coralline Algae/sugar composition wherein 50-75%, by weight, of the BETADINE was replaced with an equivalent weight of powdered Coralline Algae. The average healing time was decreased by 10% in a group of patients treated with an embodiment of Applicants' composition wherein 75-90%, by weight, of the BETADINE was replaced with an equivalent weight of powdered Coralline Algae. The average healing time was roughly equal in a group of patients treated with an embodiment of Applicants' composition wherein 90-100%, by weight, of the BETADINE was replaced with an equivalent weight of powdered Coralline Algae.

Applicant has found that the average healing time decreased about 30-35% in a group of patients treated with an embodiment of Applicants' composition wherein 5-50% of the BETADINE was replaced with an equivalent weight of powdered Coralline Algae. For example, an average healing time of 30 days using a BETADINE/sugar complex was decreased to 20 days when the BETADINE was replaced with an equivalent weight of powdered Coralline Algae.

Applicant has found that the average healing time in a group of patients treated with an embodiment of Applicant's composition comprising sugar and Coralline Algae with no BETADINE was approximately equal to the average healing time using the prior art BETADINE/sugar formulation. In addition Applicant noted additional desirable effects, wherein the average number of Iodine sensitivities was decreased by 100% compared with the typical 5-25% allergic responses resulting from use of an iodine type complex such as Betadine in a wound care formulation. Moreover, the stinging and burning sensation routinely experienced when applying the prior art iodine type complex is completely absent when using Applicant's composition comprising sugar and Coralline Algae with no iodine. In summary, Applicant has found that treating wounds with a mixture of Coralline Algae in combination with one or more sugars gives equal efficacy and fewer side effects than use of iodine-containing formulations.

In certain embodiments, Applicants' composition comprises a mixture of powdered Coralline Algae and one or more granulated or powdered sugars without any liquid carrier. In other embodiments, Applicants' composition comprises a mixture of Coralline Algae, one or more sugars (poly-saccharides), and one or more liquid carriers. In certain embodiments, the one or more liquid carriers are selected from the group consisting of water, glycerin, one or more triglyceride esters, jojoba oil, and the like.

In certain embodiments, Applicant's composition further comprises a moisture absorbing hydrophilic compound like carboxymethylcellulose, or a moisture potentiator such as one or more hydrocolloids.

In certain embodiments, Applicant's hydrocolloid is selected from the group consisting of sodium carboxymethylcellulose (NaCMC) and gelatin. In the presence of wound exudate, the one or more hydrocolloids absorb liquid and form a gel.

In various embodiments, the moisture absorbing component of Applicant's composition may be present at any weight percent loading between 0 weight percent and 85 weight percent. In each case, the weight percent loading will be selected by the treating physician based upon the location of the wound, nature of the wound, depth of the wound, age of the patient, and the like.

In certain embodiments, Applicant's composition further comprises one or more local anesthetics like benzocaine or procaine. In various embodiments, the anesthetic component of Applicant's composition may be present at any weight percent loading between 0 weight percent and 20 weight percent. In each case, the weight percent loading will be selected by the treating physician based upon the location of the wound, nature of the wound, depth of the wound, age of the patient, and the like.

FIG. 1 recites the compositional ranges, by weight percentage, for the various components of Applicant's wound care formulation. In certain embodiments, Applicant's composition comprises non-geniculate marine coral algae at a level between 0.5 weight percent and 99 weight percent. In various embodiments, the non-geniculate marine coral algae may be present at any weight percent loading between 0.5 weight percent and 99 weight percent. In each case, the weight percent loading will be selected by the treating physician based upon the location of the wound, nature of the wound, depth of the wound, age of the patient, and the like.

In certain embodiments, Applicant's composition comprises one or more sugars at a level between 1 weight percent and 99 weight percent. In various embodiments, the sugar component of Applicant's composition may be present at any weight percent loading between 1 weight percent and 99 weight percent. In each case, the weight percent loading will be selected by the treating physician based upon the location of the wound, nature of the wound, depth of the wound, age of the patient, and the like.

For example and without limitation, in certain embodiments Applicant's wound care formulation comprises 45 weight percent Coralline Algae and 50 weight percent one or more Sugars in a liquid carrier (ex. water or glycerin, etc.). In certain embodiments Applicant's wound care formulation comprises 95 weight percent Coralline Algae and 10 weight percent one or more Sugars in a liquid carrier (ex. water or glycerin, etc.). In certain embodiments Applicant's wound care formulation comprises 5 weight percent Coralline Algae and 90 weight percent one or more Sugars in a liquid carrier (ex. water or glycerin, etc.).

In certain embodiments, Applicant's one or more sugars are selected from the group consisting of one or more monosaccharides, such as for example and without limitation glucose (dextrose), fructose, galactose, and ribose. In certain embodiments, Applicant's one or more sugars are selected from the group consisting of one or more di-saccharides, such as and without limitation sucrose (table sugar), lactose, maltose, trehalose, and cellobiose. In certain embodiments, Applicant's one or more sugars are selected from the group consisting of one or more oligosaccharides. By "oligosaccharide," Applicant means a compound comprising between 3 and 10 monosaccharide moieties. In certain embodiments, each of Applicant's one or more sugars comprise a water soluble sugar.

In certain embodiments, Applicant's formulation comprises between 0 to about 80 weight percent carrier. In various embodiments, the carrier component of Applicant's composition may be present at any weight percent loading between 0 weight percent and 80 weight percent. In each case, the weight percent loading will be selected by the treating physician based upon the location of the wound, nature of the wound, depth of the wound, age of the patient, and the like.

In certain embodiments, Applicant's formulation comprises between 1 to about 80 weight percent complexing polymer. By "complexing polymer," Applicant means a water soluble polymer that when dissolved in water up to about a 10 weight percent level will stabilize iodine in that aqueous mixture up to about a 50 weight percent level.

In certain embodiments, Applicant's composition comprises one or more complexing polymers at a level between 0 weight percent and 35 weight percent. In various embodiments, the polymeric material component of Applicant's composition may be present at any weight percent loading between 0 weight percent and 35 weight percent. In each case, the weight percent loading will be selected by the treating physician based upon the iodine loading, the location of the wound, nature of the wound, depth of the wound, age of the patient, and the like.

In certain embodiments, Applicant's complexing polymer comprises polypyrrolidone I.

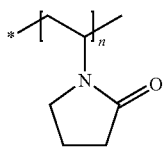

I

In certain embodiments, Applicant's complexing polymer comprises a substituted polyethyleneimine II.

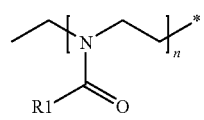

II

In certain embodiments, R1 is selected from the group consisting of methyl, ethyl, and propyl. In certain embodiments, R1 is ethyl and polymer II comprises a product sold in commerce under the trade name AQUAZOL by Polymer Chemistry Innovations, Inc., 4231 South Fremont, Tucson, Ariz.

The following examples are presented to further illustrate to persons skilled in the art how to make and use the invention. These examples are not intended as a limitation, however, upon the scope of the invention.

EXAMPLE I

Using a mixer, like an Anvil Food Machine Model MIX9120 ½ HP, 110V, 30 quart mixer, mix 30 lbs granulated white table sugar with: 1000 ml 10% Iodine complex (BETADINE); 500 ml H20; and 5 oz. powdered Coralline Algae. Stir well to desired consistency.

EXAMPLE II

Using a mixer, like an Anvil Food Machine Model MIX9120 ½ HP, 110V, 30 quart mixer, mix 30 lbs granulated white table sugar with: 500 ml 10% Iodine complex (BETADINE); 1350 ml H20; 200 gm Benzocaine; and 12.5 oz. powdered Coralline Algae. Stir well to desired consistency.

EXAMPLE III

Using a mixer, like an Anvil Food Machine Model MIX9120 ½ HP, 110V, 30 quart mixer, mix 30 lbs granulated white table sugar with: 1900 ml H20; 200 gm Benzocaine; and 12.5 oz. powdered Coralline Algae. Stir well to desired consistency.

EXAMPLE IV

Using a mixer, like an Anvil Food Machine Model MIX9120 ½ HP, 110V, 30 quart mixer, mix 5 lbs granulated white table sugar with: 317 ml H20; and 2 oz. powdered Coralline Algae. Stir well to desired consistency.

While the preferred embodiments of the present invention have been illustrated in detail, it should be apparent that modifications and adaptations to those embodiments may occur to one skilled in the art without departing from the scope of the present invention as set forth in the following claims.

I claim:

1. A composition to treat wounds, consisting of non-geniculate marine coral algae and cellobiose.

2. The composition of claim 1, wherein said non-geniculate marine coral algae comprises:
   about 0.28 weight percent calcium;
   about 0.01 weight percent magnesium.

3. The composition of claim 2, wherein:
   said calcium is present at about 279,000 ppm in said non-geniculate marine coral algae;
   carbon is present at about 124,000 ppm in said non-geniculate marine coral algae;
   iron is present at about 10,100 ppm in said non-geniculate marine coral algae;
   said magnesium is present at about 99,800 ppm in said geniculate marine coral algae; and
   silica is present at about 28,000 ppm in said non-geniculate marine coral algae.

4. The composition of claim 1, wherein said cellobiose is water-soluble.

5. The composition of claim 4, wherein:
   said non-geniculate marine coral algae is present at a level of about 0.5 weight percent; and
   said cellobiose is present at a level between of about 99.5 weight percent.

6. A composition to treat wounds, consisting of non-geniculate marine coral algae, cellobiose, and a liquid carrier.

7. The composition of claim 6, wherein said liquid carrier is selected from the group consisting of water, glycerin, one or more triglyceride esters, and jojoba oil.

8. The composition of claim 6, wherein said liquid carrier is present at a level between 0 to about 80 weight percent.

9. The composition of claim 6, wherein:
   said non-geniculate marine coral algae is present at about 45 weight percent;
   said cellobiose is present at about 50 weight percent, and
   said liquid carrier is present at about 5 weight percent.

10. The composition of claim 6, wherein:
said non-geniculate marine coral algae is present at about 5 weight percent;
said cellobiose is present at about 90 weight percent, and
said liquid carrier is present at about 5 weight percent.

* * * * *